(12) United States Patent
Sjoberg et al.

(10) Patent No.: US 8,993,525 B2
(45) Date of Patent: Mar. 31, 2015

(54) COMPOUNDS AND METHODS FOR TREATING OR PREVENTING DISEASE CONDITIONS ASSOCIATED WITH α-1-ANTITRYPSIN

(75) Inventors: Eric Richard Sjoberg, San Diego, CA (US); Gary Lee, West Windsor, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 13/879,160

(22) PCT Filed: Oct. 14, 2011

(86) PCT No.: PCT/US2011/056335
§ 371 (c)(1),
(2), (4) Date: Jun. 5, 2013

(87) PCT Pub. No.: WO2012/051518
PCT Pub. Date: Apr. 19, 2012

(65) Prior Publication Data
US 2013/0252906 A1    Sep. 26, 2013

Related U.S. Application Data

(60) Provisional application No. 61/393,181, filed on Oct. 14, 2010.

(51) Int. Cl.
| | | |
|---|---|---|
| *A61K 38/48* | (2006.01) | |
| *A61K 38/55* | (2006.01) | |
| *C07C 231/06* | (2006.01) | |
| *C07K 5/103* | (2006.01) | |
| *C07K 7/06* | (2006.01) | |
| *C12Q 1/37* | (2006.01) | |
| *A61K 38/00* | (2006.01) | |

(52) U.S. Cl.
CPC .............. *C07C 231/06* (2013.01); *C07K 5/1013* (2013.01); *C07K 7/06* (2013.01); *C12Q 1/37* (2013.01); *A61K 38/00* (2013.01); *G01N 2333/8125* (2013.01); *G01N 2333/966* (2013.01); *G01N 2500/02* (2013.01)
USPC ........................................................ 514/20.4

(58) Field of Classification Search
CPC ......... A61K 38/00; A61K 31/192; C07K 5/00
See application file for complete search history.

(56) References Cited

U.S. PATENT DOCUMENTS

2005/0203019 A1* 9/2005 Conn .............................. 514/12
2009/0232812 A1* 9/2009 Kufe et al. ................. 424/136.1

* cited by examiner

*Primary Examiner* — Marcela M Cordero Garcia
*Assistant Examiner* — Kaipeen Yang
(74) *Attorney, Agent, or Firm* — McCarter & English, LLP

(57) ABSTRACT

Pharmacological chaperone compounds and methods for the treatment of an individual having, or at risk of having, a disease condition associated with alpha-1-antitrypsin by using said compounds are disclosed. In particular, such methods are useful for the treatment or prevention of lung disorders associated with alpha-1-antitrypsin deficiency as well as liver disorders associated with an excess of alpha-1-antitrypsin. Suitable pharmacological chaperones include peptides and low-molecular weight compounds. Also provided is an assay for determining whether a test compound modulates alpha-1-antitrypsin activity.

11 Claims, 16 Drawing Sheets

Figure 1. Alpha-1-antitrypsin elastase inhibition assay
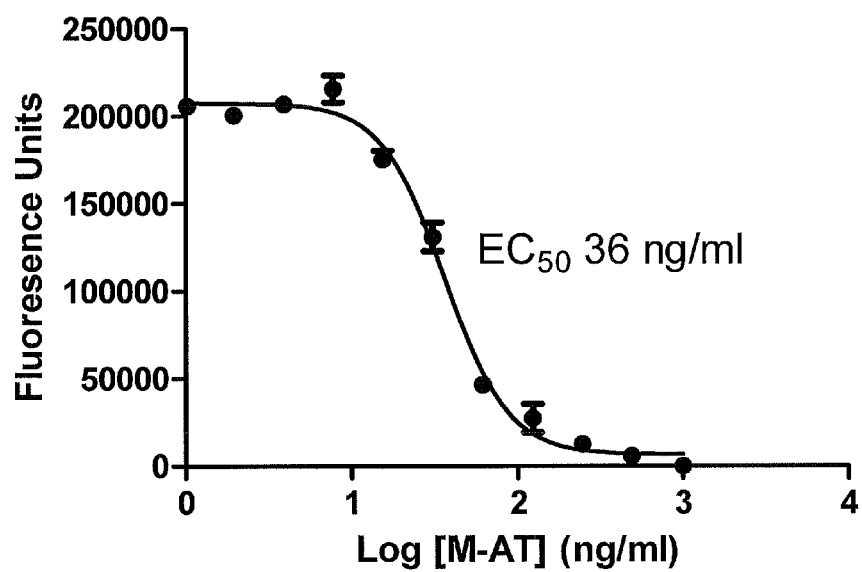

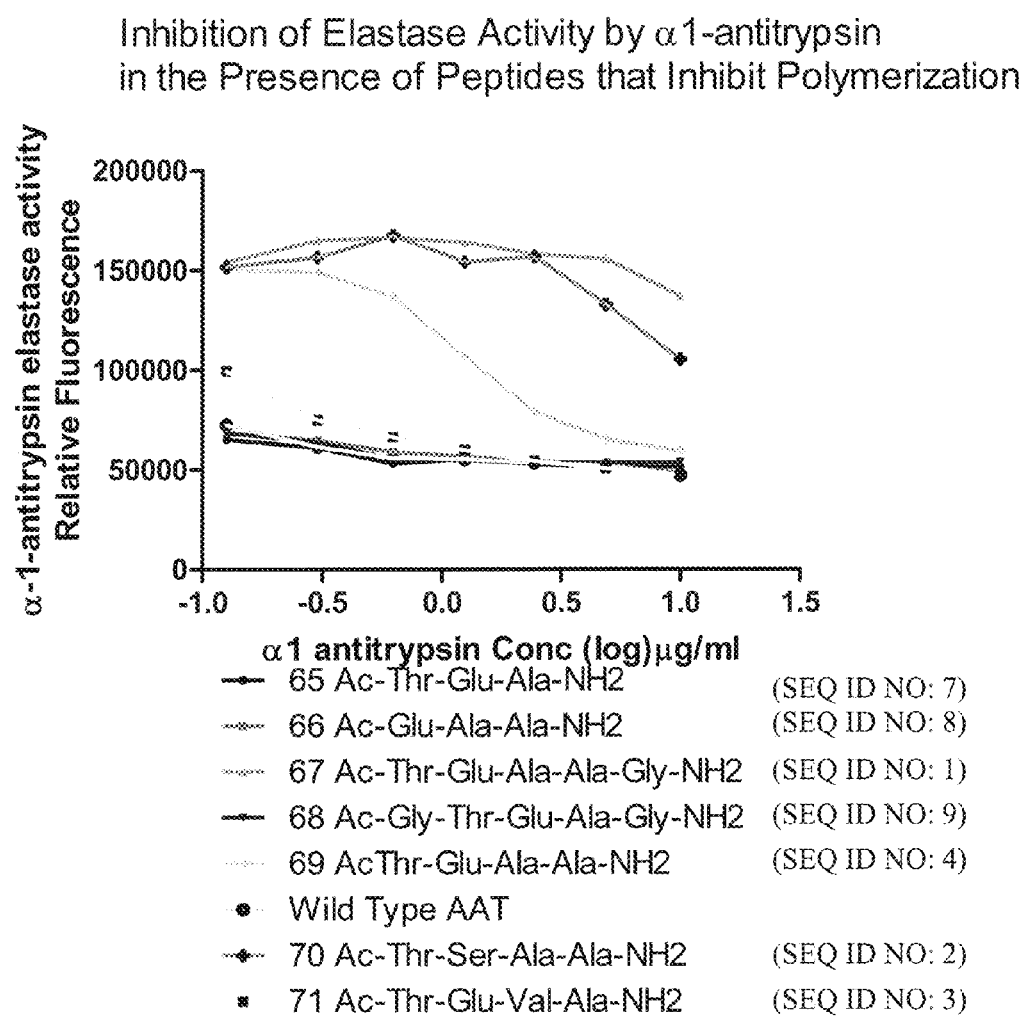

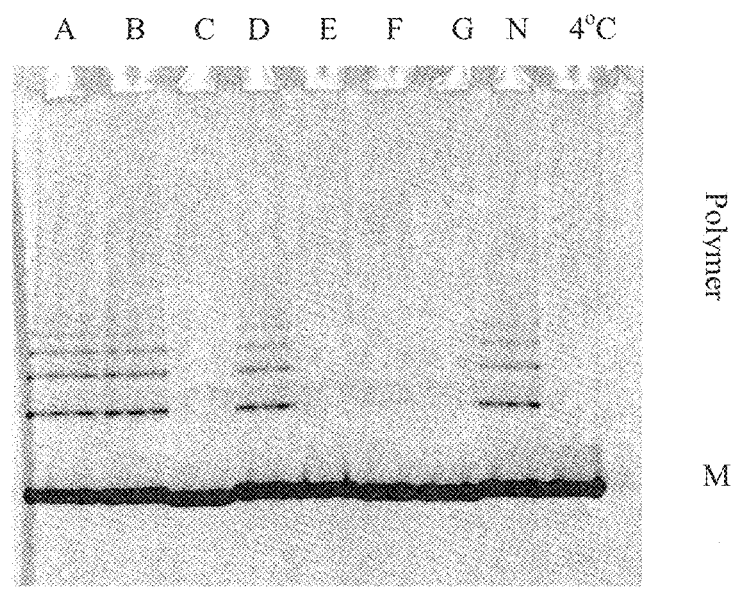
Figure 3: S4a Peptide Staircase Library-Effects on Polymerization
A: Ac-Thr-Glu-Ala-NH2 (SEQ ID NO: 7)
B: Ac-Glu-Ala-Ala-NH2 (SEQ ID NO: 8)
C: Ac-Thr-Glu-Ala-Ala-Gly-NH2 (SEQ ID NO: 1)
D: Ac-Gly-Thr-Glu-Ala-Ala-NH2 (SEQ ID NO: 10)
E: Ac-Thr-Ser-Ala-Ala-NH2 (SEQ ID NO: 2)
F: Ac-Thr-Glu-Val-Ala-NH2 (SEQ ID NO: 3)
G: Ac-Thr-Glu-Ala-Ala-NH2 (SEQ ID NO: 4)
N: No peptide Figure 4. ELISA analysis of cell line media
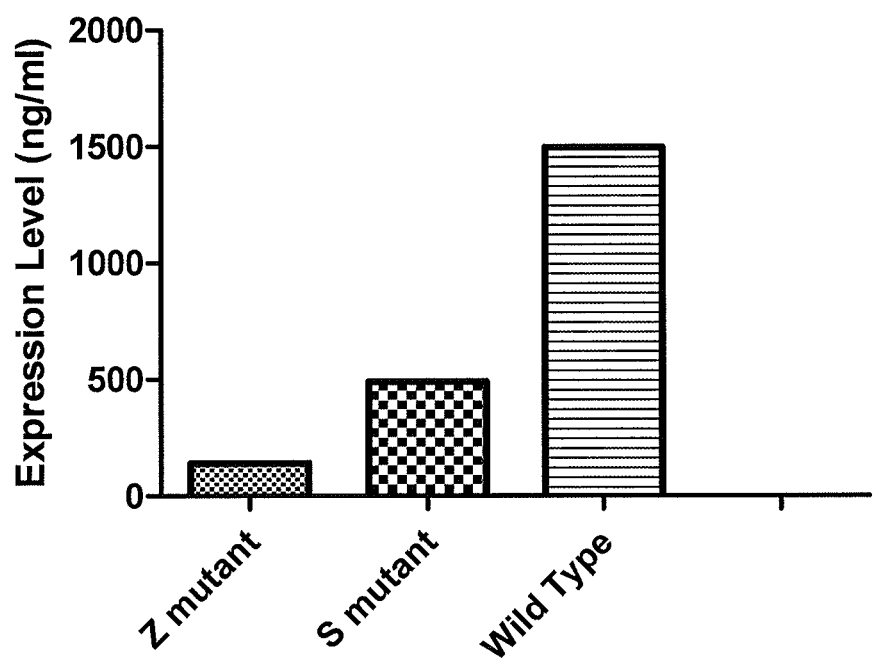

Figure 5: Alpha-1-antitrypsin elastase inhibition assay for M, S and Z alleles
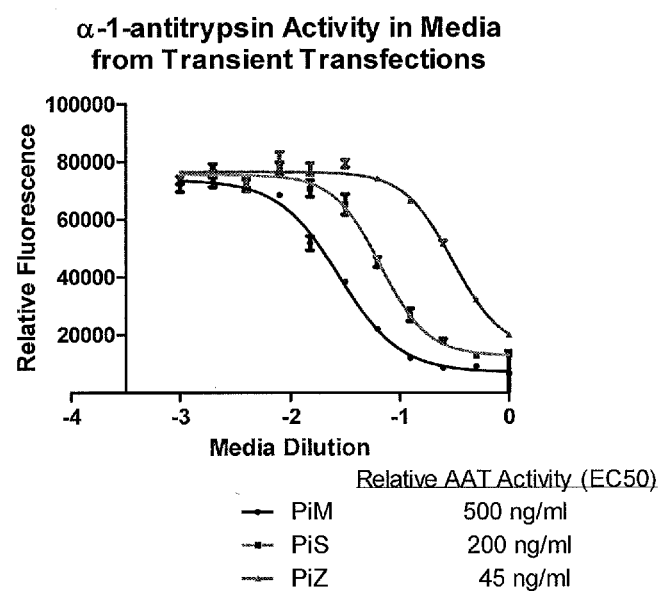

Figure 6. Western Blot of lysates and media from SF-CHO and HeLa inducible Z-AT expressing cell lines
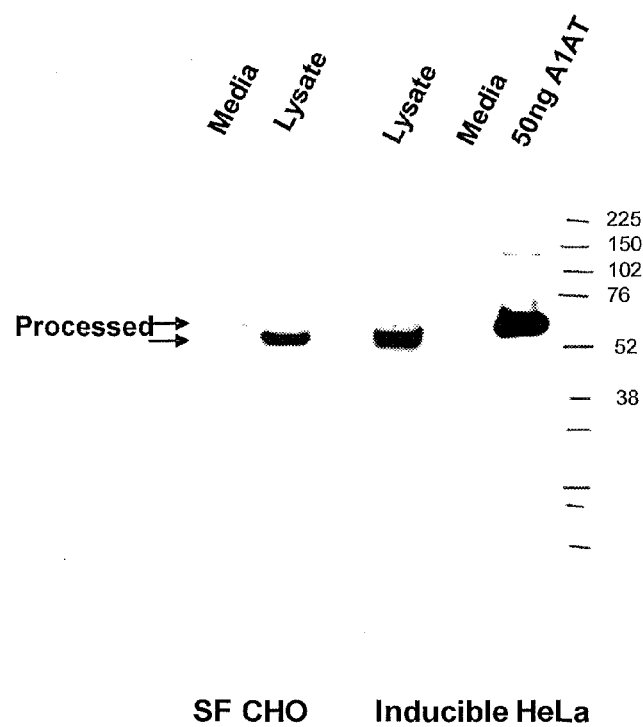

Figure 7: Computational Simulation of Ac-TEVA-NH2 (SEQ. ID NO: 3)

Figure 8: AAT, Z-AT Mutant and Double Cysteine Mutation
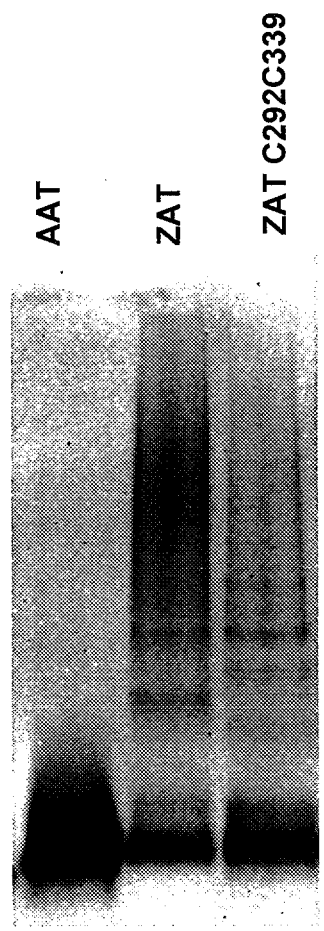

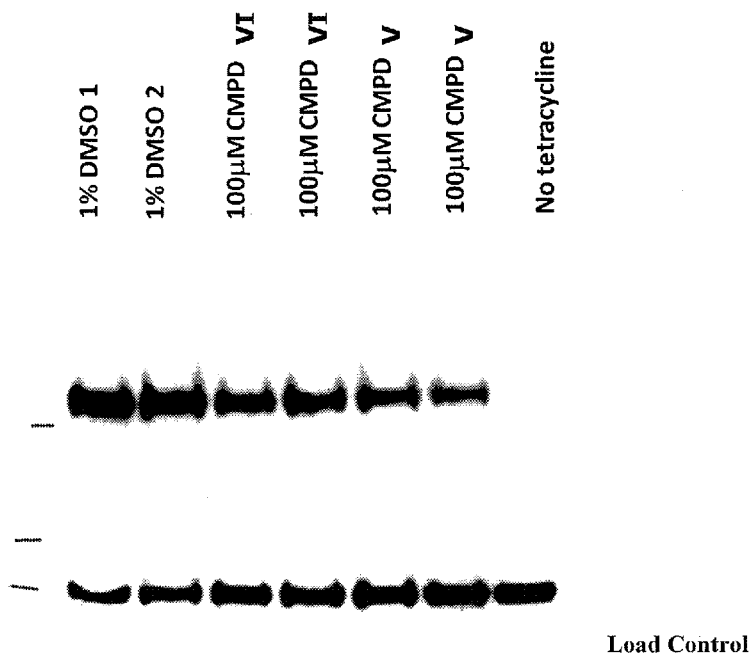
Figure 9: Intracellular levels of ZAT after treatment with Compounds V and VI 100µM Treatment
Load Control Figure 10: Intracellular levels of ZAT after treatment with Compounds V and VI 1mM Treatment
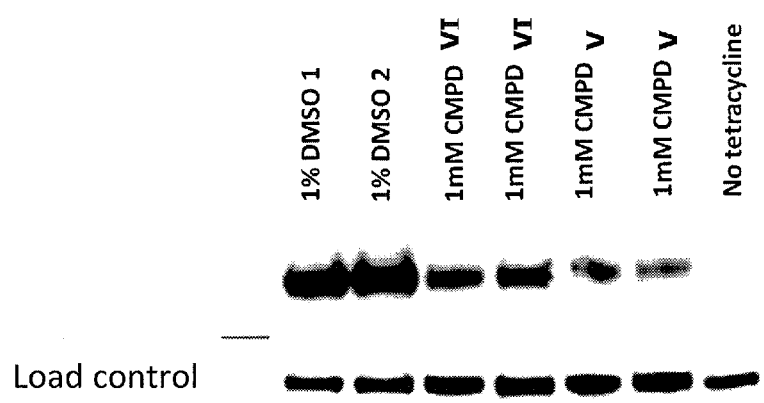

Figure 11: Extracellular Levels of ZAT and α-1-antitrypsin Activity in ZAT Inducible CHO Cells Treated With Compound V
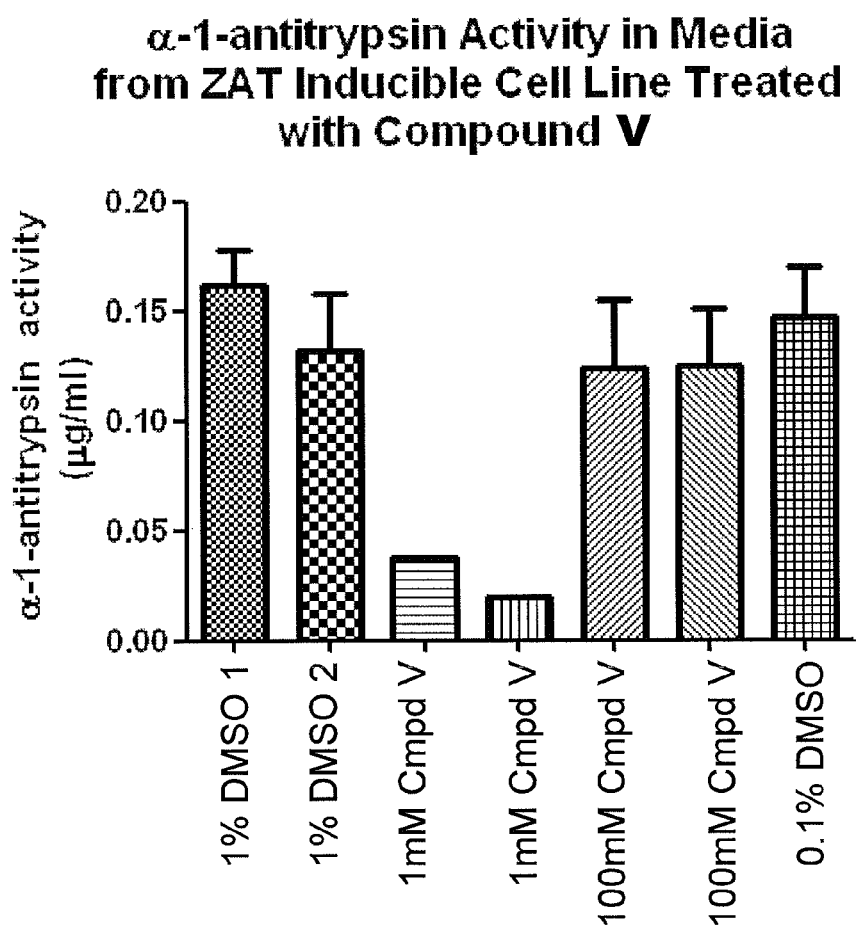

Figure 12: Extracellular Activity of ZAT 1mM Treatment
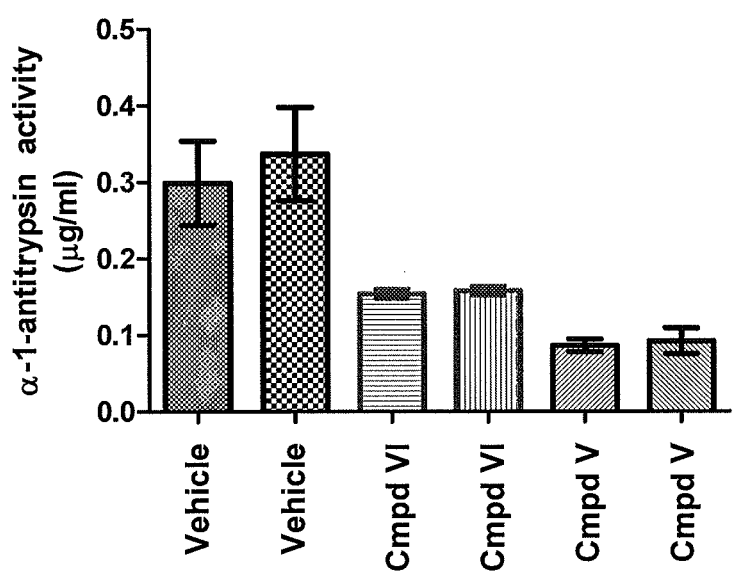

Figure 13: Intracellular Levels of ZAT after 1mM Treatment
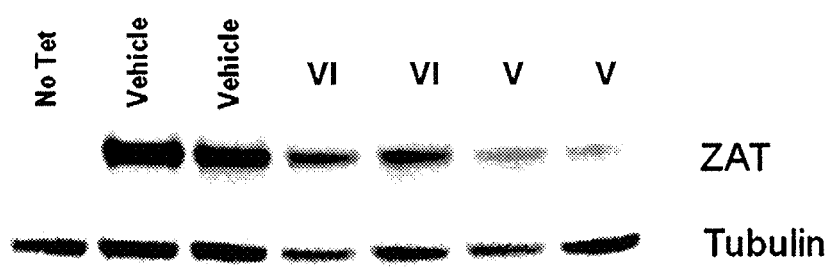

Figure 14: Intracellular Levels of ZAT after 1mM Treatment with Compounds V and VI
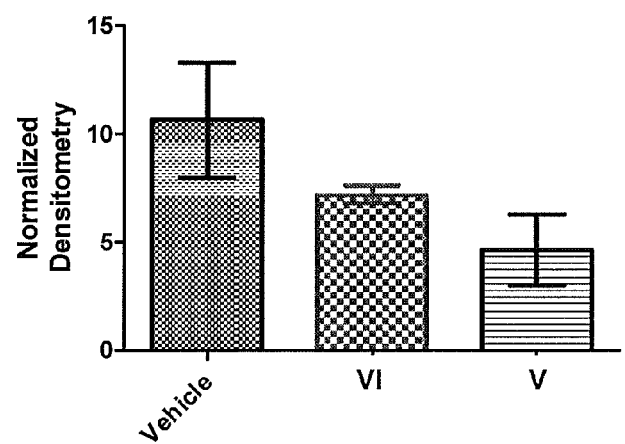

Figure 15: In Vitro Polymerization Assay
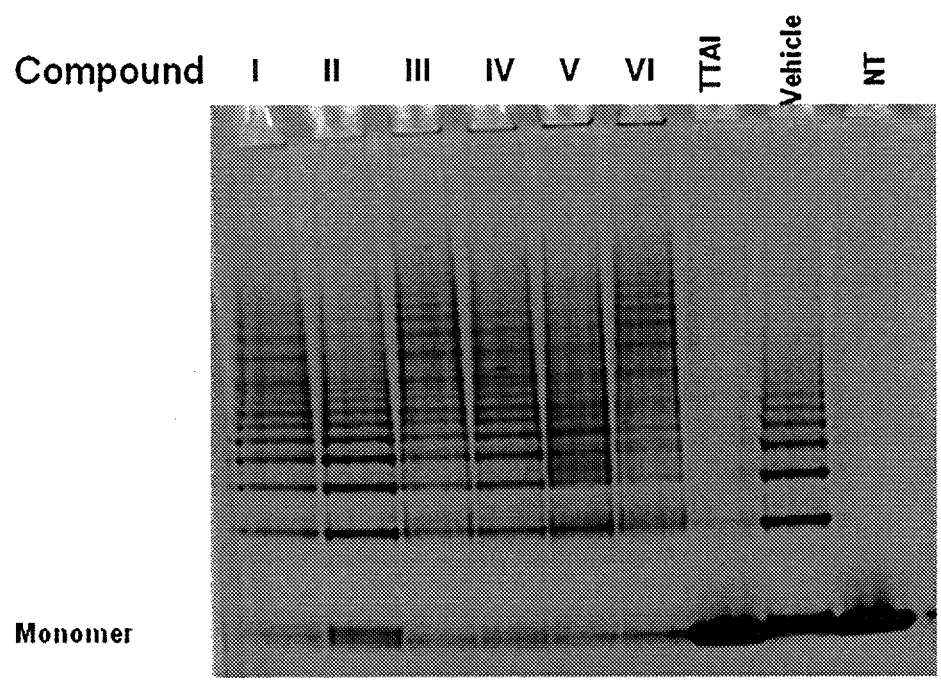

Figure 16: Computational Simulation of Compound I
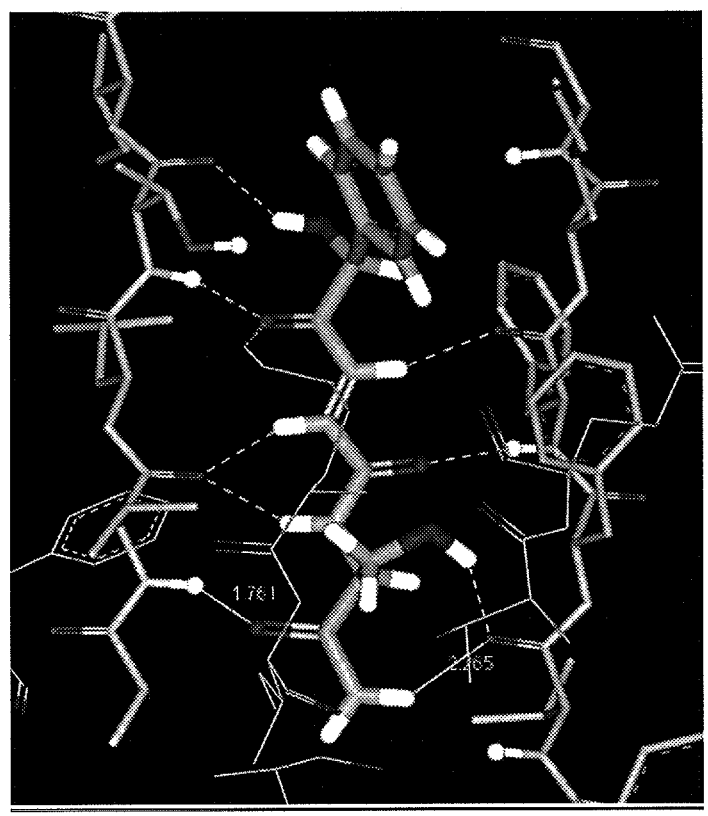

COMPOUNDS AND METHODS FOR TREATING OR PREVENTING DISEASE CONDITIONS ASSOCIATED WITH α-1-ANTITRYPSIN

This application is a 371 of International Application No. PCT/US2011/056335, filed Oct. 14, 2011, which claims the benefit of U.S. Provisional Application No. 61/393,181, filed Oct. 14, 2010. Each of the above-referenced applications are hereby incorporated by reference in their entirety.

FIELD OF THE INVENTION

The present invention relates to compounds and methods of using the same for treating and/or preventing disease conditions associated with α-1-antitrypsin.

BACKGROUND

Many human genetic disorders are caused by mutations that impair protein folding and trafficking. Even though the mutated proteins may be produced in normal amounts and may even be functionally competent, problems can arise because the mutated proteins do not fold properly and/or are not processed and trafficked correctly. Consequently, such proteins do not reach their intended cellular location and tend to accumulate in the endoplasmic reticulum (ER) or other organelles where they are prone to aggregation. The relative importance of these contributions to cellular dysfunction and disease varies among diseases, and may even differ from patient to patient and potentially from cell type to cell type. There are some conditions where loss of protein function is the primary cause of disease, and others for which a toxic-gain-of function is caused by aggregation, and excessive ER retention is the primary source of pathology. In the case of α-1-antitrypsin deficiency, both loss-of-function and toxic-gain-of-function contribute to disease pathology.

Alpha-1-antitrypsin is a protein made in hepatocytes and secreted from the liver into the blood where it functions to limit neutrophil elastase activity in the lung. A deficiency in α-1-antitrypsin can lead to emphysema, as a result of increased degradation of lung connective tissue. In many patients, alpha-1-antitrypsin deficiency is caused by a E342K missense mutation therein, referred to as the Z mutant (Z-AT). The quality control mechanisms of the ER lead to retention and accumulation of Z-AT in hepatocytes, causing damage to the liver and reducing plasma levels of alpha-1-antitrypsin as a result of reduced secretion into the blood. Thus, lung disease associated with alpha-1-antitrypsin deficiency is caused by a loss-of-alpha-1-antitrypsin function, while liver disease occurs when the Z-AT accumulates to toxic levels in liver cells (toxic-gain-of-function). Since monomeric Z-AT retains the same specific activity as wild type α-1-antitrypsin (M-AT), treatment strategies that increase secretion of Z-AT by reducing its ER retention should protect against both liver and lung damage.

Studies have demonstrated that some compounds, such as 4-phenylbutyric acid, can increase secretion of Z-AT from cells. Additionally, some small peptides (e.g., Ac-TTAI-NH$_2$) and citrate have been shown to block in vitro polymerization of Z-AT. However, the use of such osmolytes to promote protein folding is very limited as they require very high cellular concentrations and lack target specificity. Desirably, to effect protein folding and secretion in vivo, a compound must be able to penetrate the ER of liver cells, have a high affinity for Z-AT, and block polymerization thereof with minimal toxicity and side effects.

Current therapy for conditions associated with α-1-antitrypsin deficiency is limited to protein replacement therapy with M-AT derived from human plasma, typically dosed on a weekly basis. While such therapy is effective for lung pathology including emphysema, it has no effect on liver disease caused by the accumulation of polymerized Z-AT in the ER of hepatocytes. For the 10-15% of homozygotes for Z-AT afflicted with early-onset liver disease including cirrhosis and hepatocellular carcinoma, liver transplantation is the only treatment option available. Furthermore, accumulation of polymerized Z-AT in lung epithelium has a chemoattractant effect on neutrophils, which may cause further destruction of connective lung tissue. Thus, there is a need for therapeutics and methods that address disease conditions associated with both alpha-1-antitrypsin deficiency as well as toxic accumulation of alpha-1-antitrypsin.

SUMMARY

The present invention provides compounds and methods for using these compounds to treat an individual having or at risk of having a disease condition associated with alpha-1-antitrypsin comprising administering to the individual an effective amount of a pharmacological chaperone. In particular, such methods are useful for the treatment and/or prevention of lung disorders associated with alpha-1-antitrypsin deficiency. Such methods are also useful for the treatment and/or prevention of liver disorders associated with an excess of alpha-1-antitrypsin. The present invention also provides an assay for determining whether a test compound modulates alpha-1-antitrypsin activity.

BRIEF DESCRIPTION OF THE FIGURES

FIG. 1 shows a dose response curve from an alpha-1-antitrypsin elastase inhibition assay.

FIG. 2 shows inhibition of elastase activity by alpha-1-antitrypsin in the presence of peptides that inhibit polymerization.

FIG. 3 is a Western blot with Z-AT exposed to one of several acetylated peptides or control (no peptide), wherein the degree of alpha-1-antitrypsin polymerization is evident.

FIG. 4 is a graph illustrating the level of human alpha-1-antitrypsin detected by ELISA in media from cultured cells expressing the Z mutant form, S mutant form or wild type (M) form of human alpha-1-antitrypsin.

FIG. 5 is a graph of elastase activity by measuring the relative fluorescence versus concentration of inhibitor.

FIG. 6 shows a Western Blot of lysates and media from SF-CHO and HeLa inducible Z-AT expressing cell lines.

FIG. 7 is a computational simulation of Ac-Thr-Glu-Val-Ala-NH2, illustrating 11 hydrogen bonds between s5a and s3a of beta-sheet A.

FIG. 8 shows a Western Blot of wild type, Z mutant and the double cysteine Z mutant of alpha-1-antitrypsin polymerization.

FIG. 9 shows a Western Blot of the intracellular levels of ZAT in ZAT inducible CHO cells after treatment with compound V and VI at 100 μM.

FIG. 10 shows a Western Blot of the intracellular levels of ZAT in ZAT inducible CHO cells after treatment with compounds V and VI at 1 mM.

FIG. 11 shows extracellular levels of alpha-1-antitrypsin activity in media for ZAT inducible cell lines treated with compound V.

FIG. 12 shows extracellular activity of ZAT after 1 mM treatment with compounds V and VI.

FIG. 13 shows a Western Blot of intracellular levels of ZAT after 1 mM treatment with compounds V and VI.

FIG. 14 is a graph of normalized densitometry, showing intracellular levels of ZAT after 1 mM treatment with compounds V and VI.

FIG. 15 shows an in vitro polymerization assay, showing polymerization of ZAT after treatment with compounds I-VI and Ac-TTAI-NH2.

FIG. 16 is a computational simulation of compound I forming hydrogen bonds between strands s3a and s5a.

DETAILED DESCRIPTION

The present invention provides compounds, known as pharmacological chaperones, and methods for using these compounds to prevent and/or treat disease conditions associated with alpha-1-antitrypsin. Pharmacological chaperones include peptides and small molecules, which selectively bind to a target protein and increase protein stability and/or proper trafficking thereof such that the target protein can pass the ER quality control system and function at its proper site. Thus, the administration of a pharmacological chaperone can increase protein levels and cellular activity of the target protein. Additionally, administration of a pharmacological chaperone reduces ER accumulation of the target protein as well as aggregation thereof and associated stress on cells.

Though not meant to be limited by any theory with the subject invention, the compounds of the present invention are believed to bind to a site on alpha-1-antitrypsin, (specifically, the A beta-sheet 4, more specifically P8-4 of the reactive center loop) and thereby abolish polymerization of alpha-1-antitrypin. Furthermore, non-acetylated forms of such compounds are believed to dissociate from alpha-1-antitrypsin.

Definitions

Listed below are definitions of various terms used to describe this invention. These definitions apply to the terms as they are used throughout this specification, unless otherwise limited in specific instances, either individually or as part of a larger group.

As used herein, "α-1-antitrypsin," or "alpha-1-antitrypsin" or "AAT" refers to a protease inhibitor which inhibits elastase, among other proteases.

As used herein, "disease condition associated with α-1-antitrypsin" refers to an autosomal genetic disorder leading to an accumulation of α-1-antitrypsin and/or deficiency of α-1-antitrypsin in one or more organs such that toxic levels of α-1-antitrypsin activity and/or a deficiency of α-1-antitrypsin activity results. Diseases associated with α-1-antitrypsin include, but are not limited to, cirrhosis, chronic obstructive pulmonary disease, pneumothorax, asthma, Wegener's granulomatosis, pancreatitis, gallstones, bronchiectasis, pelvic organ prolapse, primary sclerosing cholangitis, autoimmune hepatitis, emphysema (predominantly involving the lower lobes and causing bullae), cancer (including hepatocellular carcinoma (liver), bladder carcinoma, gallbladder cancer, lymphoma and lung cancer).

As used herein, "Z mutation" refers to the E342K (Glu342Lys) missense mutation, which causes alpha-1-antitrypsin deficiency. The mutated form of alpha-1-antitrypsin can be abbreviated as "ZAT" or "Z-AT."

As used herein, "MAT" refers to wild-type alph-1-antitrypsin protein, produced by the so-called normal allele.

As used herein, "treating" means to ameliorate one or more symptoms associated with the referenced disorder.

As used herein, "preventing" means to mitigate a symptom of the referenced disorder.

As used herein, "an effective amount" means an amount effective to prevent and/or treat a patient at risk for developing or diagnosed with the referenced disorder, and thus producing the desired therapeutic effect.

Furthermore, where "R" is used, it is understood by a person of ordinary skill in the art that R, $R_2$, $R_3$, etc. will not be selected such that an unstable molecule will result.

α-1-Antitrypsin Activity Assay

An elastase inhibition assay was developed to measure the effects of a test compound on the inhibitory activity of secreted Z-AT. In one embodiment, to detect elastase activity, bovine elastin was labeled with BODIPY, which causes the fluorescence of the conjugate to be quenched. This non-fluorescent substrate was digested by elastase to yield highly fluorescent fragments. Alternatively, the non-fluorescent substrate may be digested by another protease to yield fluorescent fragments. The activity of α-1-antitrypsin was monitored by measuring a decrease in fluorescent signal, indicative of the elastase inhibitory activity of α-1-antitrypsin. A test compound was added to determine its effect on the elastase inhibitory activity of α-1-antitrypsin. In one embodiment, the resulting fluorescence was monitored in a Perkin Elmer Victor V plate reader using absorption and emission filters for fluorescein (435/535 nm).

Cell Based Assays

Serum Free CHO Cell Lines.

Serum free CHO cell lines were developed, expressing M-AT, Z-AT (Glu342Lys) and the S mutation (Glu264Val), so that secreted alpha-1-antitrypsin activity could be measured directly from media without interference from bovine, alpha-1-antitrypsin introduced into the media from serum. Briefly, cDNA was isolated by PCR from first strand human liver cDNA using conventional cloning methods. The Z-AT and S-AT mutations were generated using Quick Change mutagenesis kit according to the manufactures (Stratagene) instructions. Plasmids expressing M-AT, Z-AT or S-AT under control of the CMV promoter were transfected into CHO cells that were adapted to serum free conditions. This cell-based model makes it possible to ascertain the ability of a test compound to effect alpha-1-antitrypsin activity by ascertaining the impact on elastase inhibitory activity of alpha-1-antitrypsin in media from cultured cells. ELISA and activity levels of alpha-1-antitrypsin both indicate that Z-AT is secreted into the media at concentrations 10-fold below M-AT corresponding to the decrease in levels observed in PiZZ homozygote patients.

The media and lysates from the Z-AT and M-AT cell lines were analyzed on a native gel followed by western blotting to determine the extent of polymerization. Z-AT that is secreted into the media from the serum free CHO line is essentially all polymerized. While lysates from Z-AT and M-AT cell lines do contain a small percentage of monomeric alpha-1-antitrypsin, the majority of material is polymerized. In contrast, monomeric M-AT was detected from wild type cell line as expected.

In addition, inducible CHO and HeLa cell lines expressing Z-AT and M-AT have been generated for screening purposes. While the inducible CHO cell line secretes Z-AT, the HeLa inducible cell line retains essentially all the Z-AT intracellularly, as shown in FIG. 6.

Analysis of Intracellular and Extracellular Z-AT in Constitutive and Inducible Cell Lines Additional cell lines to screen for pharmacologic chaperones and to identify surrogate markers of Z-AT expression were developed using an inducible promoter system. The inducible systems are useful for determining if particular chaperones need to be present prior to Z-AT translation in the endoplasmic reticulum to induce secretion of Z-AT and/or inhibit The detection limit of this embodiment of the assay for α-1-antitrypsin is approximately 16 ng/ml and the fluorescence was relatively insensitive to pH between a pH of about 3 to a pH of about 9. FIG. 1 displays a typical dose response curve using increasing concentrations of M-AT and an elastase concentration of about 2.5 mU/ml. This level of sensitivity for detecting the activity of α-1-antitrypsin is particularly important when screening numerous test compounds, since relatively small cell numbers are typically used for cell based screening assays. FIG. 5 also uses this assay to compare activity of cells transiently transfected with α-1-antitrypsin M, S and Z alleles.

Human Alpha-1-Antitrypsin Specific ELISA.

An ELISA that is commercially available (Alpco) was tested for sensitivity and specificity to human M-AT to test for stimulation of Z-AT secretion from cells and plasma in vivo. Testing confirmed that this ELISA assay is highly specific for human alpha-1-antitrypsin and has no cross reactivity with mouse serum. The level of detection for this assay is 3-4 ng/ml. The sensitivity of this assay along with its specificity makes it a useful quantitative assay for cell based and in vivo testing of plasma. FIG. 4 shows the results of an ELISA analysis detecting the presence of human alpha-1-antitrypsin in media from cultured cells expressing the Z mutant form, S mutant form or wild type (M) form of alpha-1-antitrypsin.

In Vitro Polymerization Assay.

An in vitro polymerization assay was employed to screen the ability of a pharmacological chaperone to inhibit polymerization. Notably, the Z-mutation, E342K, lowers the kinetic barrier to polymerization relative to M-AT, causing the characteristic polymerization of Z-AT. In brief, M-AT or Z-AT was incubated at 37° C. for 4 hours, followed by 30 minutes at 62° C. The samples were then run on a Bis-Tris native gel and either blotted onto PVDF or detected with colloidal blue staining. Peptides at 1 mM were incubated with equal amounts (50 ng) of Z-AT for 4 hours at 37° C., followed by a 62° C. pulse for 30 minutes. Samples were separated on a 4-12% Bis-Tris native gel, blotted onto PVDF and the blot probed with a human specific antibody for alpha-1-antitrypsin. Additionally, in the case of samples from human plasma, a western blot was performed to assess the level of alpha-1-antitrypsin. polymerization. The inducible HeLa cell line retains Z-AT intracellularly as little Z-AT can be detected in the media. The Z-AT contained in lysates is apparently not processed to complex N-glycans as the molecular weight is slightly lower than M-AT purified from plasma, which is consistent with the findings of others. The intracellular material is endo H sensitive indicative of high mannose N-linked glycans.

Serum Free CHO and HeLa cells in which expression of Z-AT is under control of the tetracycline repressor were grown to confluence. To analyze the intra- and extracellular production of Z-AT, media was collected and cells were lysed in non-ionic detergent. Media and lysates were analyzed on a NuPAGE SDS gel followed by western blotting utilizing a human specific sheep anti-human alpha-1-antitrypsin polyclonal antibody.

The lack of N-linked processing in intracellular Z-AT is also clear in the serum free CHO cell line. These data demonstrate that these cell lines retain Z-AT intracellularly, most likely in the endoplasmic reticulum. Furthermore, the Z-AT that is retained or secreted is in a polymeric state based on native gels followed by western blotting. These cell lines represent useful screening tools for the identification of small molecules that inhibit polymerization and stimulate secretion of active human Z-AT.

Introduction of Disulfide Bond Between Strands s5a and s6a of Beta-Sheet A Inhibits Polymerizations of ZAT in Mammalian Cell Lines and Increases Secretion of Active ZAT There is a variant of the Z mutation which features a double cysteine mutation. In addition to the E342K mutation, there are also T339C and S292C mutations. This double cysteine mutation also shows alpha-1-antitrypsin polymerization. However, it shows less polymerization as compared to the normal Z mutation. FIG. 8 shows a western blot of the three forms. There is some polymerization in the double cysteine mutation, less than the Z mutant, but more than the wild type. Thus, introduction of a disulfide bond between strands s5a and s6a decreases polymerization of ZAT, and increases secretion of active ZAT in the media of mammalian cells (CHO and HeLa).

Peptides that Inhibit Polymerization of Z-AT

Peptides that inhibit the polymerization of Z-AT include Ac-Thr-Glu-Ala-Ala-Gly-NH2 (SEQ ID NO: 1), Ac-Thr-Ser-Ala-Ala-NH2 (SEQ ID NO: 2), Ac-Thr-Glu-Val-Ala-NH2 (SEQ ID NO: 3) and Ac-Thr-Glu-Ala-Ala-NH2 (SEQ ID NO: 4). Such peptides can be synthesized using conventional methods known to one of skill in the art. One embodiment of peptide synthesis uses standard Fmoc chemistry with peptide amide linker (PAL) resin as solid support on a peptide synthesis apparatus. After deprotection of the N-Fmoc group on a solid support with 20% (v/v) piperidine in dimethylformamide (DMF), the resin is placed in a reaction vessel. The selected amino acids are coupled to the resin in the vessel. All coupling reactions are performed in DMF at ambient temperature for 2 hrs using a 4-fold excess of Fmoc- protected amino acids relative to resin loading. Each coupling step is monitored by a ninhydrin test to ensure that the amino acids are completely incorporated into the forming peptides. After completion of coupling, the resin from the vessel is thoroughly washed, mixed, deprotected and replaced into the reaction vessel. For the acetylation on N terminus, the resin is soaked in acetic anhydride/diisopropylethylamine/DMF for 2 hrs. Final release of the peptides from the resin and side chain deprotection is concomitantly achieved with 95% (v/v) trifluoroacetic acid in water for 2 hrs. All peptides are then lyophilized three times prior to use.

FIG. 3 shows a western blot of ZAT in the presence of several acetylated peptides as well as control (no peptide). Ac-TSAA-NH2 (SEQ ID NO: 2), Ac-TEVA-NH2 (SEQ ID NO: 3), Ac-TEAA-NH2 (SEQ ID NO: 4) and Ac-TEAAG-NH2 (SEQ ID NO: 1) show significantly less alpha-1-antitrypsin polymerization as compared to the other peptide compounds wherein alpha-1-antitrypsin polymerization was similar to untreated Z-AT. The reduction of alpha-1-antitrypsin polymerization demonstrates the ability of peptides depicted in Table 1 to be used as a treatment to reduce accumulation of Z-AT in the liver.

TABLE 1

Acetylated Peptides that Inhibit Polymerization

| Structure | Name |
|---|---|
| [structure of Ac-Thr-Ser-Ala-Ala-NH2] | Ac-Thr-Ser-Ala-Ala-NH2 (Ac-TSAA-NH2) (SEQ ID NO: 2) |
| [structure of Ac-Thr-Glu-Val-Ala-NH2] | Ac-Thr-Glu-Val-Ala-NH2 (Ac-TEVA-NH2) (SEQ ID NO: 3) |
| [structure of Ac-Thr-Glu-Ala-Ala-NH2] | Ac-Thr-Glu-Ala-Ala-NH2 (Ac-TEAA-NH2) (SEQ ID NO: 4) |
| [structure of Ac-Thr-Glu-Ala-Ala-Gly-NH2] | Ac-Thr-Glu-Ala-Ala-Gly-NH2 (Ac-TEAAG-NH2) (SEQ ID NO: 1) |

Figure 7:
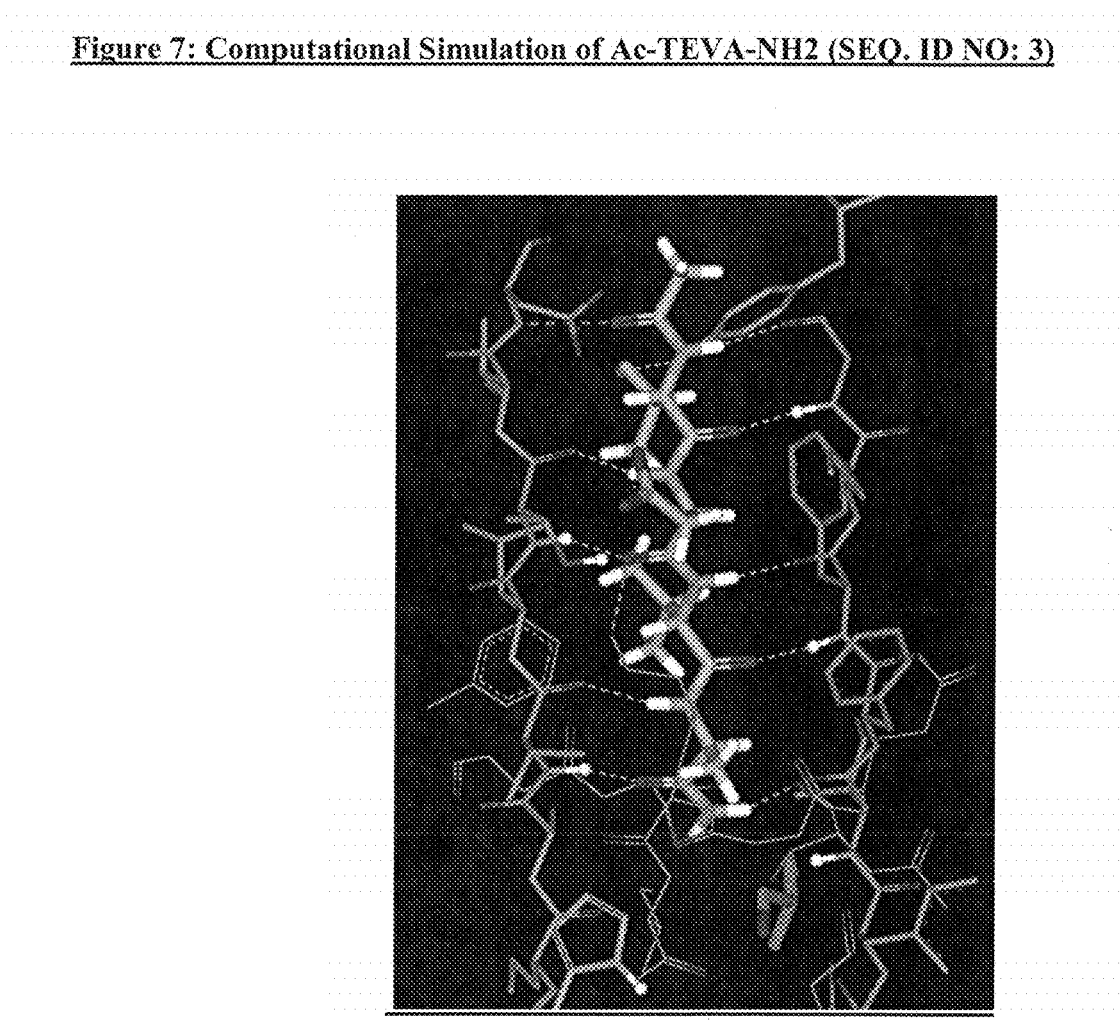

FIG. 2 shows the inhibition of elastase activity by alpha-1-antitrypsin in the presence of peptides that inhibit polymerization. The AAT assay disclosed above was used. This graph reveals that alpha-1-antitrypsin in the presence of Ac-Thr-Glu-Val-Ala-NH2 (SEQ ID NO: 3) inhibits elastase activity significantly, in fact to a level comparable to that of wild type alpha-1-antitrypsin. FIG. 7 shows a computational simulation of Ac-Thr-Glu-Val-Ala-NH2 (SEQ ID NO: 3) bound to the β-sheet using BioPredict. The simulation suggests Ac-Thr-Glu-Val-Ala-NH2 (SEQ ID NO: 3) forms eleven hydrogen bonds between the s5a and s3a strands of Z-AT. Therefore, Ac-Thr-Glu-Val-Ala-NH2 (SEQ ID NO: 3) inhibits polymerization, but does not inhibit alpha-1-antitrypsin activity at concentrations required to inhibit polymerization. Thus, Ac-Thr-Glu-Val-Ala-NH2 (SEQ ID NO: 3) could help both with aiding the removal of accumulated ZAT from the ER and allowing the ZAT to fulfill its protease inhibition function. This makes Ac-Thr-Glu-Val-Ala-NH2 (SEQ ID NO: 3) a potentially good agent to treat both liver and lung-related diseases caused by alpha-1-antitrypsin.

To increase membrane permeation and plasma stability, peptides may be cyclized. One embodiment of such a cyclization is to add a lactone group. An example of a prophetic synthetic scheme for cyclization of Ac-Thr-Thr-Ala-Thr-NH2 (SEQ ID NO: 5) by creating a macrolactone is as follows according to Scheme 1:

Scheme 1: Macrolactone of Ac-Thr-Thr-Ala-Thr-NH2 (SEQ ID NO: 3)
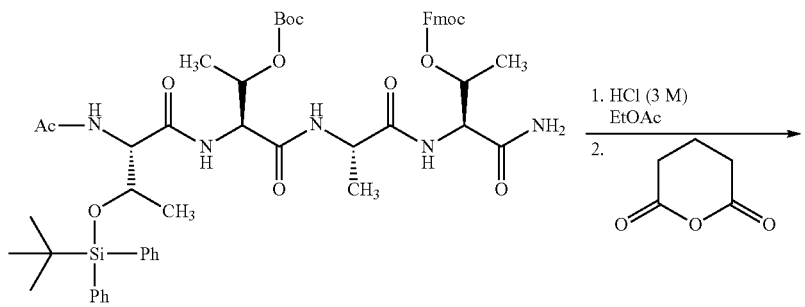
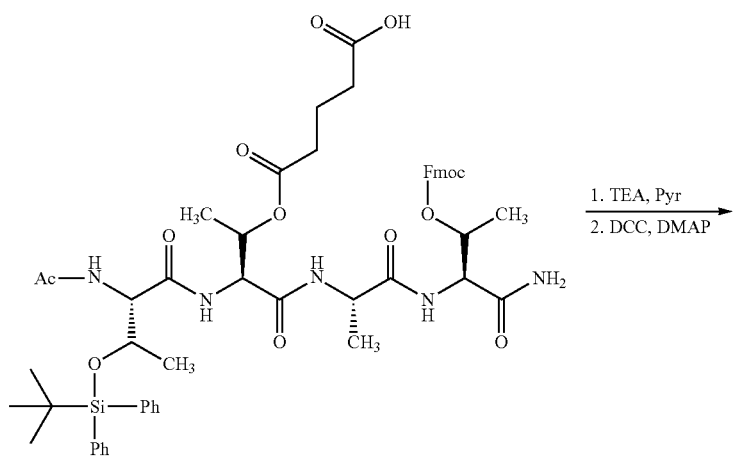
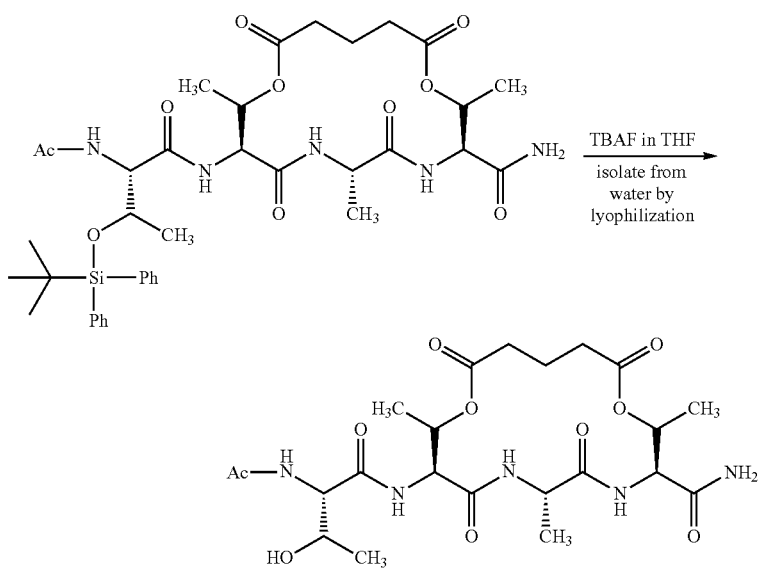

Additional Compounds

Additionally, several low molecular weight compounds (Compounds I-VI) were discovered which increase hydrogen bonding between s3a and s5a of beta-sheet A. FIG. 16 shows a computational simulation of compound I. Compound I forms seven potential hydrogen bonds between strands s3a and s5a. Furthermore, two compounds, compounds V and VI, decrease intracellular levels of ZAT. These compounds are shown in Table 2, along with structural data for each compound. FIG. 9 shows a western blot of the intracellular levels of ZAT after treatment with 100 μM of compounds V and VI. Compounds V and VI show lower levels of ZAT. Similarly, FIG. 10 shows the intracellular levels of ZAT after treatment with compounds V and VI at a concentration of 1mM. The levels of intracellular levels of ZAT are even lower when treated at the higher concentration. FIG. 11 is a graphical representation of extracellular levels of ZAT and alpha-1-antitrypsin activity in ZAT inducible CHO cells after treatment with compound V. FIG. 11 shows higher activity levels with higher treatment with compound V. FIG. 12 is a similar graph, showing extracellular activity of ZAT after 1 mM treatment with compounds V and VI. FIG. 13 depicts a western blot of intracellular levels of ZAT after 1 mM treatment. Compounds V and VI show significant reduction in ZAT levels intracellularly. FIG. 14 is a graph of showing intracellular levels of ZAT after 1 mM treatment with compounds V and VI. Levels are lower after treatment with compounds V and VI. FIG. 15 is an in vitro polymerization assay with compounds I-VI, as well as Ac-TTAI-NH2 (SEQ ID NO: 6), a vehicle control and non-treated alpha-1-antitrypsin. There is an increase in polymerization after treatment with the low-molecular weight compounds.

TABLE 2

Small Molecules That Decrease Intracellular Levels of ZAT

| Structure | | LC-MS and $^1$H-NMR Data |
|---|---|---|
| (structure image) | Compound I | $C_{12}H_{16}N_4O_5$, MW = 296; LC-MS: M + H = 297, M + Na = 319; $^1$H-NMR (600 MHz, DMSO) 9.78 (s, 1H), 8.08 (s, 1H), 7.45 (d, 2H), 7.32 (t, 2H), 7.27 (t, 1H), 7.21 (s, 1H), 7.12 (s, 1H), 6.30 (d, 1H), 6.15 (d, 1H), 5.01 (d, 1H), 4.91 (t, 1H), 4.04 (m, 1H), 3.60 (m, 1H), 3.47 (m, 1H). |
| (structure image) | Compound II | $C_{12}H_{16}N_4O_5$, MW = 296; LC-MS: M + H = 297, M + Na = 319; $^1$H-NMR (600 MHz, DMSO) 9.78 (s, 1H), 8.08 (s, 1H), 7.45 (d, 2H), 7.32 (t, 2H), 7.27 (t, 1H), 7.21 (s, 1H), 7.12 (s, 1H), 6.30 (s, 1H), 6.15 (d, 1H), 5.01 (d, 1H), 4.91 (t, 1H), 4.04 (m, 1H), 3.60 (m, 1H), 3.47 (m, 1H) |
| (structure image) | Compound III | $C_{13}H_{18}N_4O_5$, MW = 310; LC-MS: M + H = 311, M + Na = 333; $^1$H-NMR (600 MHz, DMSO) 9.79 (s, 1H), 8.12 (s, 1H), 7.45 (d, 2H), 7.32 (t, 2H), 7.27 (t, 1H), 7.09 (d, 2H), 6.18 (s, 2H), 5.01 (d, 1H), 4.92 (d, 1H), 4.03 (m, 1H), 3.92 (m, 1H), 0.98 (d, 3H). |
| (structure image) | Compound IV | $C_{13}H_{18}N_4O_5$, MW = 310; LC-MS: M + H = 311, M + Na = 333; $^1$H-NMR (600 MHz, DMSO) 9.80 (s, 1H), 8.12 (s, 1H), 7.45 (d, 2H), 7.32 (t, 2H), 7.27 (t, 1H), 7.09 (d, 2H), 6.17 (s, 2H), 5.01 (d, 1H), 4.92 (d, 1H), 4.03 (t, 1H), 3.93 (m, 1H), 1.00 (d, 3H). |

TABLE 2-continued

Small Molecules That Decrease Intracellular Levels of ZAT

| Structure | | LC-MS and $^1$H-NMR Data |
|---|---|---|
| [Structure of Compound V] | Compound V | $C_{13}H_{18}N_4O_7$, MW = 342; LC-MS: M + H = 343, M + Na = 365; $^1$H-NMR (600 MHz, DMSO) 9.66 (s, 1H), 8.89 (s, 1H), 8.05 (s, 1H), 7.22 (d, 1H), 7.12 (s, 1H), 6.87 (s, 1H), 6.82 (t, 2H), 6.30 (s, 1H), 5.95 (s, 1H), 4.92 (s, 1H), 4.86 (d, 1H), 4.04 (m, 1H), 3.74 (s, 3H), 3.60 (t, 1H), 3.49 (m, 1H). |
| [Structure of Compound VI] | Compound VI | $C_{14}H_{20}N_4O_7$, MW = 356; LC-MS: M + H = 357, M + Na = 379; $^1$H-NMR (600 MHz, DMSO) 9.66 (s, 1H), 8.89 (s, 1H), 8.09 (s, 1H), 7.10 (s, 1H), 7.08 (s, 1H), 6.87 (s, 1H), 6.82 (m, 2H), 6.19 (s, 1H), 5.96 (s, 1H), 4.91 (m, 1H), 4.86 (d, 1H), 4.02 (m, 1H), 3.94 (m, 1H), 3.73 (s, 3H), 1.01 (m, 3H). |

Synthesis

Scheme 2 shows one process specifically for the synthesis of compounds III and IV. However, it is easily modified for other low molecular weight compounds, including compounds I, II, V and VI by starting with the corresponding starting material noted in Table 3 below. To a solution of methanol (50 ml), $SOCl_2$ (10 ml) was added dropwise at 0° C., the solution was allowed to stir for 1 hr at room temperature, then threonine (5.1 g, 42.9 mmol) was added, the mixture was stirred for 7 hrs at 38° C. and concentrated to dryness, the crude product was purified by re-crystallization form petroleum ether (5 ml) and ether (1 ml) to afford pure product 12-M-1 (5.0 g; yield: 88%).

To a solution of 12-M-1 (7.3 g, 42.9 mmol) and $K_2CO_3$ (14.8 g, 107 mmol) in THF (100 ml), $(Boc)_2O$ (11.2 g, 51.5 mmol) was added dropwise at 0° C., the solution was allowed to stir for 3 hrs at room temperature, then the solution was concentrated to dryness to get the crude product, the crude product was purified by silica gel chromatography eluted with (EtOAc: PE=1:4) to give product 12-M-2 (9.9 g; yield: 99%) as oil.

The solution of 12-M-2 (233 mg, 1.0 mmol) in methanol amine solution (10 ml), the solution was allowed to stir over night at 0° C., then the solution was concentrated to dryness to get the crude product 12-M-3, the crude product was used directly for the next step without purification.

To a solution of 12-M-3 and pyridine (119 mg, 1.5 mmol) in THF (10 ml), Fmoc-Cl (280 mg, 1.1 mmol) was added dropwise at 0° C., the solution was allowed to stir for 4 hrs at room temperature, then the solution was concentrated to dryness to get the crude product, the crude product was purified by silica gel chromatography eluted with (EtOAc: PE=1:10) to give product 12-M-4 (394 mg; yield: 89.6%) as white solid.

To a solution of 12-M-4 (390 mg, 0.80 mmol) in DCM (5 ml), TFA (2.5 ml) was added dropwise, the solution was stirred for 4 hrs at room temperature, then the solution was concentrated to dryness to get the crude product 12-M-5, the crude product was used directly for the next step without purification.

To a solution of 12-M-5 in DCM (15 ml), saturated solution of sodium bicarbonate (6 ml) was added, the solution was stirred for 20 mins. Then triphosgene (89 mg, 0.3 mmol) was added at 0° C. and the solution was stirred for 20 mins at 0° C. The mixture was extracted with DCM (20 ml), the organic layers was dried and concentrated to dryness to get the crude product 12-M-6, the crude product was used directly for the next step without purification.

To a solution of (S)-methyl 2-hydroxy-2-phenylacetate (2.4 g, 14.5 mmol) in methanol (15 ml), hydrazine hydrate (4.6 g, 150 mmol) was added dropwise, the solution was allowed to stir for 4 hrs at room temperature, then the solution was concentrated and extracted with DCM, the organic phase was dried over $Na_2SO_4$ and evaporated to dryness to get the crude product, the crude product was purified by silica gel chromatography eluted with (DCM: MeOH=20:1) to give product 12-M-7 (1.0 g; yield: 42%) as white solid.

A solution of 12-M-6 and 12-M-7 (100 mg, 0.6 mmol) in DCM (25 ml) was refluxed for 2 hrs, then the solution was stirred over night at room temperature. The solution was concentrated to dryness to get the crude product, the crude product was purified by silica gel chromatography eluted with (DCM: MeOH=10:1) to give product 12-M-8 (150 mg; yield: 47%) as white solid. LC-MS: $[M+H]^+$=533, $[M+Na]^+$= 555 ($C_{28}H_{28}N_4O_7$ MW=532).

A solution of 12-M-8 (60 mg) and piperidine (0.5 ml) in DCM (20 ml) was stirred for 10 mins at room temperature. The solution was concentrated to dryness to get the crude product, the crude product was purified by silica gel chromatography eluted with (DCM: MeOH=10:1) to give compound III and IV.

Scheme 2: Synthesis of Compounds
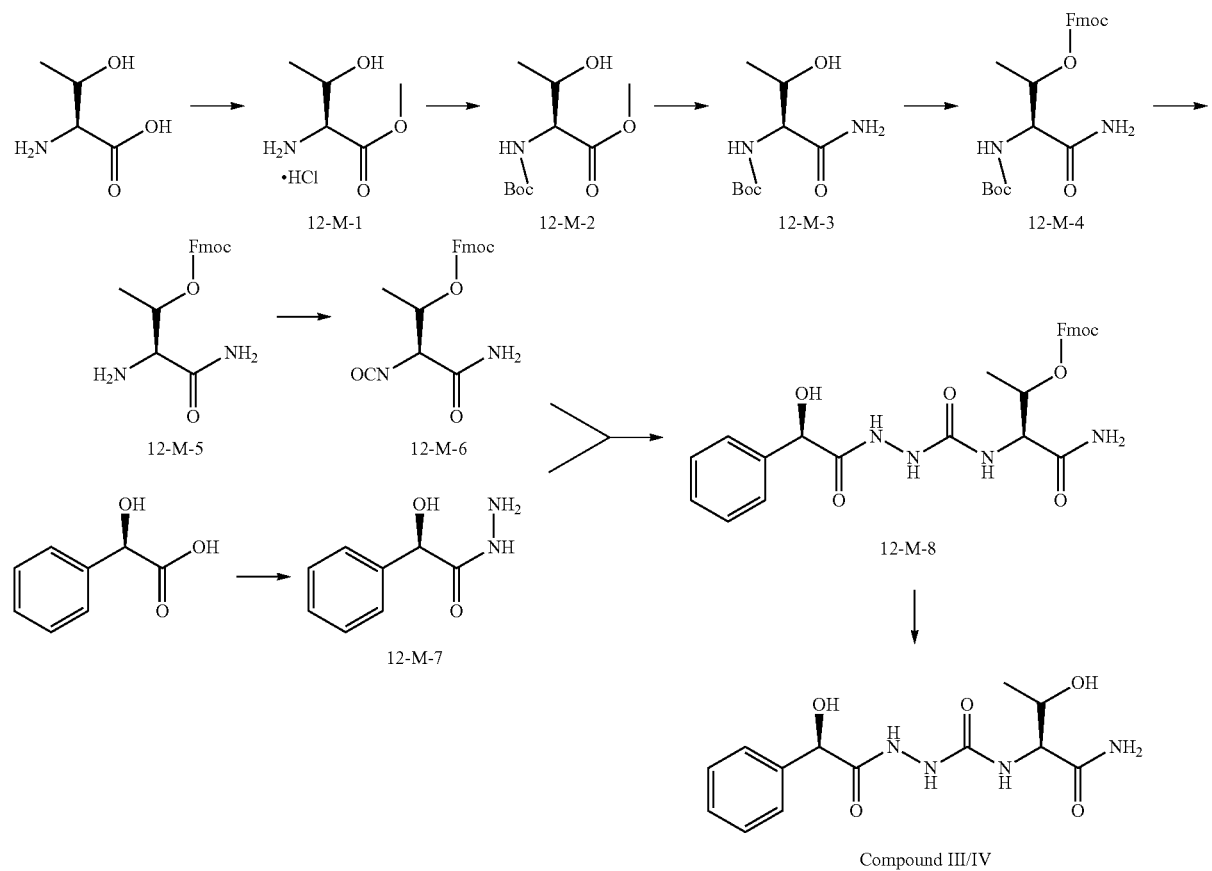
| TABLE 3 | |
|---|---|
| Compounds for Synthesis | |
| Name | Structure |
| Benzyloxycarbonyl chloride | |
| L-Alaninamide hydrochloride | |
| L-Serinamide hydrochloride | |
| L-Threoninamide hydrochloride | |
| TABLE 3-continued | |
|---|---|
| Compounds for Synthesis | |
| Name | Structure |
| R-(−)-Mandelic acid | |
| S-(+)-Mandelic acid | |
| 4-methoxy-3-hydroxymandelic acid | |

The invention claimed is:
1. A compound according to the structure:

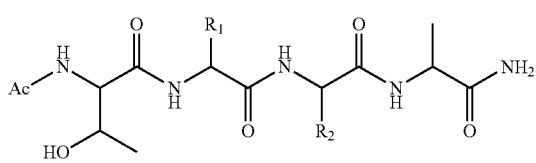

wherein:
R1 is —(CH$_2$)$_2$—COOH or —CH$_2$—OH
R2 is —CH$_3$ or —CH—(CH$_3$)$_2$.
2. The compound of claim 1, wherein R1 is —CH$_2$—OH and R2 is —CH$_3$.
3. The compound of claim 1, wherein R1 is —(CH$_2$)$_2$—COOH and R2 is —CH—(CH$_3$)$_2$.
4. The compound of claim 1, wherein R1 is —(CH$_2$)$_2$—COOH and R2 is —CH$_3$.
5. A compound according to the structure:

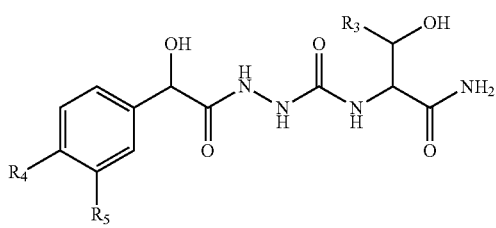

wherein
R$_3$ is —H or —CH$_3$
R$_4$ is —H or —OCH$_3$
R$_5$ is —H or —OH.

6. The compound of claim 5 having the structure:

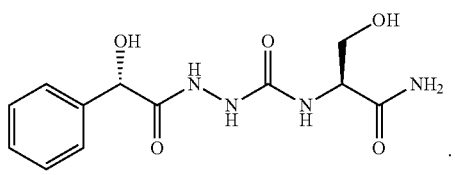 [SMILES: NC(=O)[C@H](CO)NC(=O)NNC(=O)[C@@H](O)c1ccccc1]

7. The compound of claim 5 having the structure:

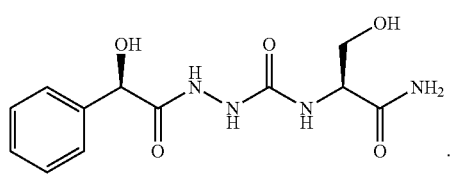 [SMILES: NC(=O)[C@H](CO)NC(=O)NNC(=O)[C@H](O)c1ccccc1]

8. The compound of claim 5 having the structure:

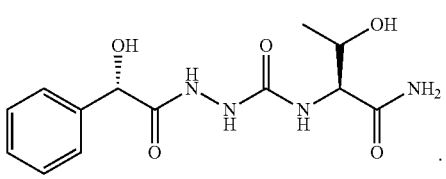 [SMILES: CC(O)[C@H](NC(=O)NNC(=O)[C@@H](O)c1ccccc1)C(N)=O]

9. The compound of claim 5 having the structure:

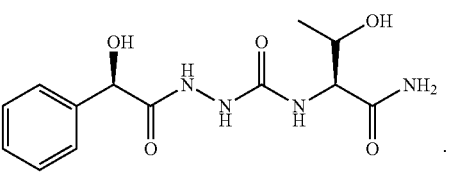 [SMILES: CC(O)[C@H](NC(=O)NNC(=O)[C@H](O)c1ccccc1)C(N)=O]

10. The compound of claim 5 having the structure:

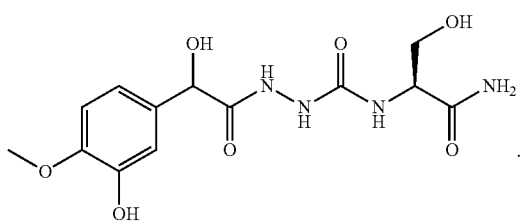 [SMILES: COc1ccc(C(O)C(=O)NNC(=O)N[C@@H](CO)C(N)=O)cc1O]

11. The compound of claim 5 having the structure:

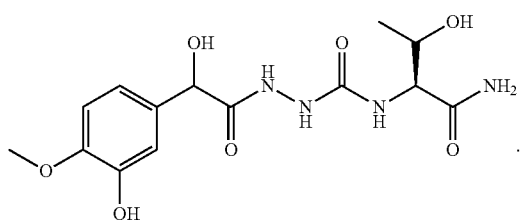 [SMILES: COc1ccc(C(O)C(=O)NNC(=O)N[C@H](C(N)=O)C(C)O)cc1O]

* * * * *

SEQUENCE LISTING

<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Glu Ala Ala Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Ser Ala Ala
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Glu Val Ala
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Glu Ala Ala
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Thr Ala Thr
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic

```
                           peptide

<400> SEQUENCE: 6

Thr Thr Ala Ile
1

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Glu Ala
1

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Ala Ala
1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Thr Glu Ala Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Thr Glu Ala Ala
1               5
```